US00PP13128P2

(12) United States Plant Patent
Probasco

(10) Patent No.: US PP13,128 P2
(45) Date of Patent: Oct. 29, 2002

(54) HOP PLANT NAMED 'MILLENNIUM-48'

(75) Inventor: Eugene G. Probasco, Yakima, WA (US)

(73) Assignee: John I. Haas, Inc., Washington, DC (US)

( * ) Notice: Subject to any disclaimer, the term of this patent is extended or adjusted under 35 U.S.C. 154(b) by 0 days.

(21) Appl. No.: 09/392,628

(22) Filed: Sep. 9, 1999

(51) Int. Cl.[7] ..... A01H 5/00
(52) U.S. Cl. ..... Plt./236
(58) Field of Search ..... Plt./236

(56) References Cited

U.S. PATENT DOCUMENTS

| | | | | |
|---|---|---|---|---|
| PP8,812 | P | 6/1994 | Probasco | Plt./100 |
| PP8,823 | P | 7/1994 | Probasco | Plt./100 |
| PP8,824 | P | 7/1994 | Probasco | Plt./100 |
| PP9,511 | P | 4/1996 | Tanikoshi et al. | Plt./100 |
| PP10,147 | P | 12/1997 | Probasco | Plt./100 |
| PP10,956 | P | 6/1999 | Lewis et al. | Plt./236 |

OTHER PUBLICATIONS

John I. Haas, Inc., "Hop Varieties" brochure, Sep. 1997.*
Haunold et al., "Registration of 'Nugget' Hop", Crop Science 24(3):618, 1984.*
Haunold, et al., "Nugget, A New Hop Cultivar with High Alpha–Acids Potential", Journal of the American Society of Brewing Chemists, (1984), vol. 42, No. 2: 62–64.
Haunold, "Hop" In Hybridication of Crop Plants, (1980) ch. 27: 393–405.
Langer, et al., "Cannabinaceae", Agricultural Plants, (1981), ch. 8: 190–193.
Romanko et al., "Registration of Galena Hop", Crop Science, Jul./Aug. 1979, 19(4): 563.

* cited by examiner

*Primary Examiner*—Bruce R. Campell
*Assistant Examiner*—Anne Marie Grünberg
(74) *Attorney, Agent, or Firm*—Morgan, Lewis & Bockius

(57) ABSTRACT

A new and distinct triploid hop, *Humulus lupulus*, plant named 'Millennium-48' selected from the progeny of tetraploid 'Nugget'×proprietary line No. '833-53M', characterized by a high yield and resistance to powdery mildew. Harvest maturity is late, similar to 'Nugget' and following 'Galena' by about 1 week.

2 Drawing Sheets

BACKGROUND AND SUMMARY OF THE INVENTION

Hops (*Humulus lupulus*) are grown commercially for use in flavoring beers, stouts and ales. Lupulin glands found inside female hop cones provide the resins and essential oils which are the primary components of the hop flavor each variety imparts to beers, stouts and ales. New hop varieties are evaluated for their growing characteristics, per acre hop cone yields (dried to approximately 8% moisture), the chemical composition of the resins and essential oils contained within the hop cone's lupulin glands, and the unique flavor each variety imparts to beers, stouts and ales. Only female hop plants produce cones containing lupulin glands, and thus only female hop plants have any commercial value. Male hop plants have no commercial value other than for use in breeding programs to create new varieties.

This invention relates to a new and distinct variety of hop and more particularly to an asexually reproduced hop variety selected from among hop plants resulting from a controlled cross pollination between a tetraploid 'Nugget' female hop plant with an unpatented proprietary male hop plant '833-53M'.

'Nugget' is an unpatented diploid high alpha acids variety released in 1983 from the U.S.D.A. breeding program in Oregon (Haunold et al., 1984, *J. Am. Soc. Brewing Chemists* 42(2):62–64; Haunold et al., 1984, *Crop Science* 24(3):618). 'Nugget' is characterized by mild aroma, a low proportion of cohumulone in the alpha acids with good storage stability of alpha acids. The inventor used colchicine to produce the tetraploid 'Nugget' which was the female parent used to produce the novel variety of this invention.

Proprietary male hop plant '833-53M' originated from a controlled cross pollination in 1982 between unpatented female hop plant U.S.D.A. Accession No. 21055 and unpatented male hop plant U.S.D.A. Accession No. 63015M.

The controlled cross pollination program resulting in the creation of the new hop selection called 'H900448-8,' was performed in 1989 by the inventorin a greenhouse located at Yakima, Wash. 'H900448-8' was discovered by the inventor in 1991 growing among the hop plants which were produced from the seeds resulting from the controlled cross pollination program described above.

The seeds from the cross between the tetrapolid 'Nugget' female hop plant and proprietary male hop plant '833-53M' were planted in a greenhouse in 1990. The most vigorous plants resulting from the cross were selected and planted in 1990 in a hop field located at Toppenish, Wash.

In 1991, as a result of chemical analysis and field observations of the hop plants, the inventor selected the 'H900448-8' hop plant for further evaluations based on its unusually high percentage of alpha-acids, coupled with a resonable projected per acre cone yield. The per acre cone yield projections were based upon the cone production of the single 'H900448-8' hop plant observed in 1991. The 'H900448-8' plant was not asexually reproduced in 1991. In 1992, the 'H900448-8' plant was observed again in the same location and production of alpha-acids was again high.

In 1993, second (2nd) generation rootstock from the 'H900448-8' variety were planted in a four plant test plot located at Toppenish, Wash. and an eight plant test plot in the Willamette Valley in Oregon. Data were collected and observations were made on these small test plots during the 1994, 1995, 1996, 1997 and 1998 growing seasons. The data confirmed the unusually high alpha-acids percentage and acceptable yield levels characteristic of 'H900448-8'.

In 1998, second (2nd) and third (3rd) generation rootstock from the 'H900448-8' variety were planted in a larger test plot of approximately 15 acres (large acreage test plot) at hop farms located at Mabton and Toppenish, Wash. Additional acreage was added in 1999 for brewing trials.

All of the testing and evaluation of the growing characteristics, per acre hop cone yield, analytical data and alpha-acids extraction tests were carried out on hop farms, laboratory facilities, and industrial extraction facilities under the inventor's direction.

Based upon the field observations performed, and chemical analytical data collected during this testing and evaluation program from 1991 through 1998, it appears that second (2nd) and third (3rd) generation 'H900448-8' hop plants demonstrate genetic stability with respect to the new variety's novel characteristic of unusually high alpha-acids yields. Also, the new 'H900448-8' variety demonstrates genetic stability with respect to the production of commercially viable per acre hop cone yields.

Harvest dates of the variety 'H900448-8' are medium-late, usually ready to pick approximately one week later than Galena and about the same time as Nugget in the Toppenish area. The compact and ovoid to conic shape cones of this variety are mid to large in size and this aids in the ease of picking and cleaning. Adaptation to mechanical harvesting is very good, the cones detach easily from stems and leaves do not develop in the cones. The cones do not shatter during harvest. 'Millennium-48' is the cultivar name for the hop selection previously designated as 'H900448-8' during the experimental testing of the variety.

BRIEF DESCRIPTION OF THE DRAWINGS

The accompanying photographs illustrate the new 'Millennium-48' variety.

DETAILED DESCRIPTION OF THE PREFERRED EMBODIMENTS

Figure 1:
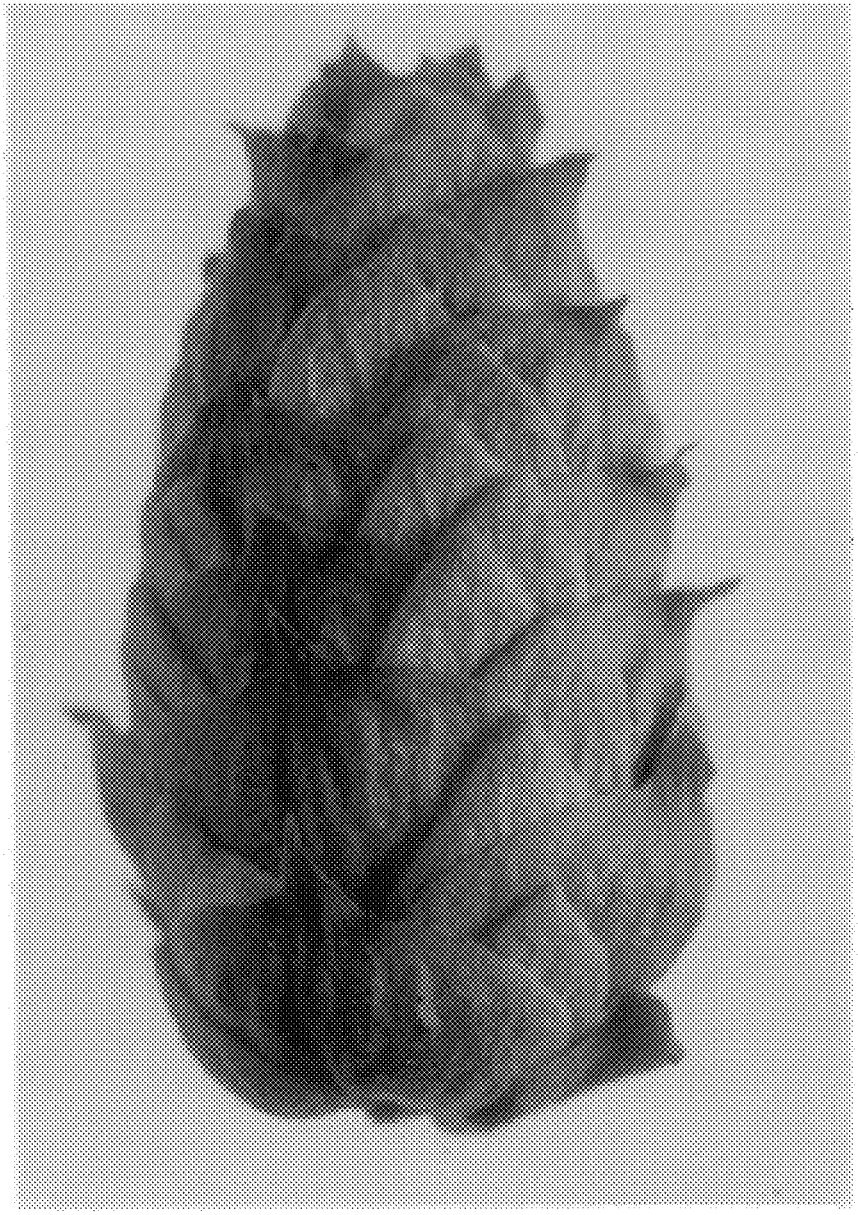
FIG. 1 illustrates a close up of a single cone.
Figure 2:
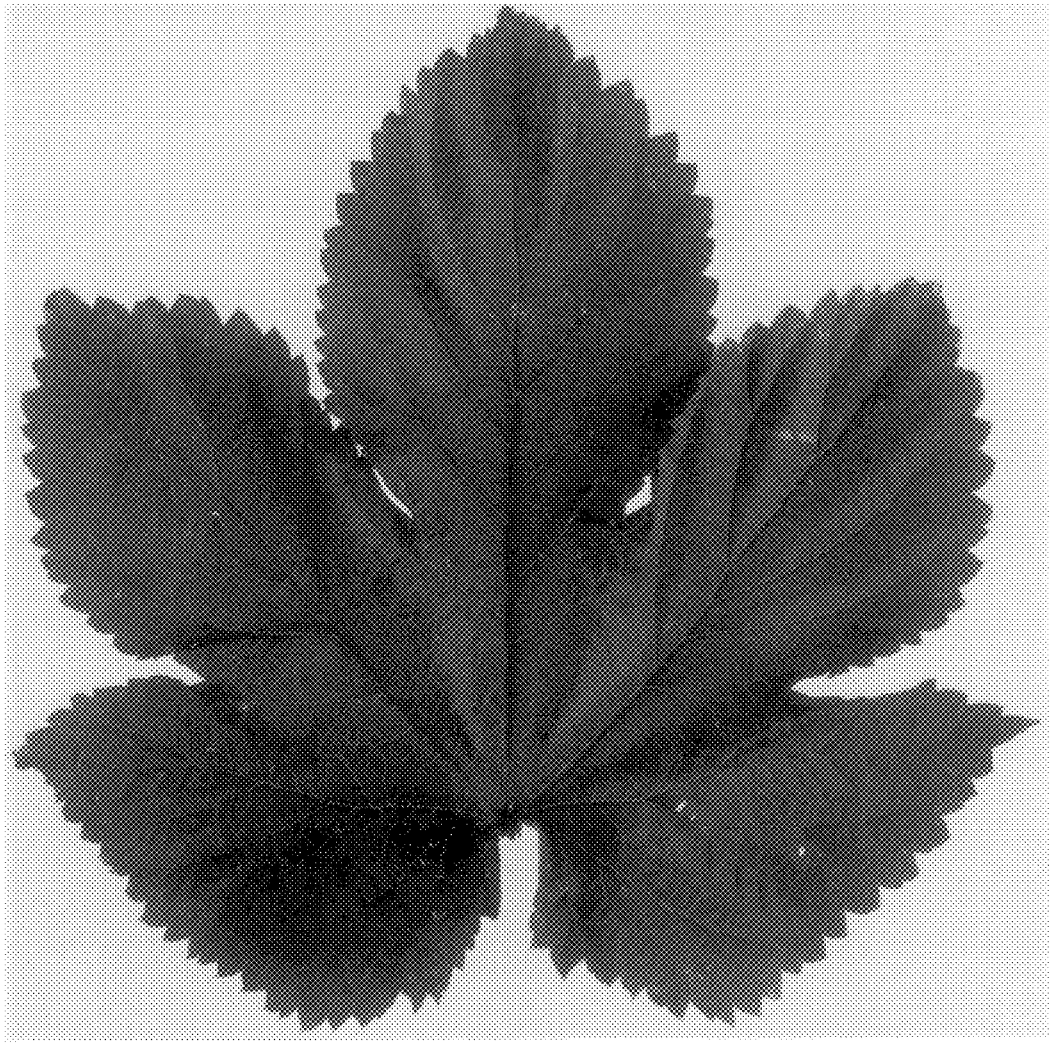
FIG. 2 illustrates the leaf close up.

This description contains information about certain botanical and analytical chemical characteristics upon which the hop industry relies in identifying and distinguishing specific hop varieties. The analytical data used to describe this new variety are subject to some variation among different samples of this new variety, due to the maturity of the hop cones sampled, climatic and growing conditions, geography, and other variables. For these reasons the analytical values used to describe this new variety are expressed in terms of ranges or averages of values rather than absolute or fixed values.

GENERAL DESCRIPTIVE INFORMATION

I. Introduction

The hop plant, *Humulus lupulus L.,* is a perennial plant which produces annual climbing bines and a perennial crown. In the spring, the buds which have developed on the crown send out numerous shoots. The annual shoots are referred to as bines or vines and can grow up to 25 feet in a single growing season. These bines climb in a clockwise direction without the aid of tendrils, but rather with the aid of hooked hairs known as tricomes. The bine of a mature hop may be one half to three quarters of an inch thick at the six foot height. Laterals grow from the axillary buds at each node along the main bine. The inflorescences develop from the axils of the laterals and each inflorescence becomes a single hop cone at maturity.

II. Roots

The hop crown will become woody with age, developing heavy, rough bark after the first year. Much of the hop crown consists of branched stem tissue which lies buried at a shallow depth below the surface of the soil. The stem tissue, or rhizome, produces buds which in the spring develop into a mass of heterophyllous shoots. The crown also produces two types of roots—horizontal and vertical. The horizontal roots are fibrous, adsorptive roots used for water uptake. The vertical roots, which develop from the horizontal roots, are thick and fleshy and serve as carbohydrate storage organs.

III. Stems

The annual stems grow from the crown in early spring and twine around suitable supports. Shoots of 'Millennium-48' emerge from winter dormancy about the same time as the commercial variety Galena which is approximately the last week of March or first week of April in the State of Washington. The stems are hexagonal in shape with the corners of the hexagon often protruding. Early in the growing season the shoots are purple, however, as the season progresses the main stem color is green and has a dark green or purple stripe. On all sides of the stem are hairs, consisting mostly of silicates, and as these harden they become one or two sided hooks. Generally, the size of the stem at the six foot height is between ⅜ to ½ in diameter.

The first training for the variety 'Millennium-48' is ideally the middle days of May. "Training" of the vines is a term used by growers which means placement of vines on a support, which has one end attached on the 18' trellis wire and the other end secured into the soil. During training, the vines are placed on the support in a clockwise manner which is the natural helical growth pattern of all hop varieties. 'Millennium-48' has good vigor and can reach the top of the trellis in 5–6 weeks after training.

IV. Leaves

Leaves of 'Millennium-48' are borne in pairs at each node on the main bine and the majority of these leaves are opposite in arrangement. Located at the petiole base of each leaf is a stipule which is interpetiolar in arrangement. The bine leaves are cordate in shape with mostly 5 lobes and have palmate venation. The leaf margins are serrate to dentate. Leaf color is green on the upper surface and lighter green on the lower surface. Stiff fine hairs on the upper surface of the leaf produce a dull appearance and rough texture. The lower surface bears many disc-shaped yellowish resin glands. The leaves are petiolate and the petioles are slightly channeled, therefore having a flat surface on the upper side. The leaf petiole extends from the main vine in a reflexed position.

V. Laterals

The laterals, or sidearms as they are often called, originate from buds in the axils of leaves of the main bine. The lateral position is "caulous" which means it grows more or less evenly spaced along the main bine.

VI. Cones

The inflorescences of 'Millennium-48' begin to appear in late June and mature during the second or third week of September. As they mature, they form a conelike structure, or strobile, referred to as a "cone". These inflorescences develop on a cranked axis and the cones form in pairs or clusters. The cones develop on the laterals from the top of the plant to approximately 48 inches above the ground. The cone consists of a central rachis or strig which bears numerous bracts and bracteoles. At the base of each bracteole is an ovary which if fertilized by pollination, results in the lengthening and thickening of the central strig. Flowers of this variety cannot be fertilized because the plant's genetic make-up is triploid.

The aroma of hop cones of any variety is not measurable and therefore, highly subjective. Aroma descriptions are not useful because of this subjectivity. However, the intensity of hop aroma is less debatable and for this variety could be described as medium.

The hop cone of 'Millennium-48' is conic in shape and is tight when referring to its compactness. The tip of the cone is mostly pointed. The bract tip shape is cuspidate to mucronate, while the bracteole tip shape is acute to rounded. The central rachis or strig is thick compared to the strig of the variety Cluster. The cone and more specifically the bracteoles, contain numerous lupulin glands. As the top cone matures, the lupulin glands fill and form a globular shape and are golden yellow in color. One of the most important components of these resins is the alpha-acids which give beer its bitterness, but other components of the lupulin glands also contribute to the flavor of the beer.

The cone numbers, size and weight are direct factors in determining the yield of this variety, as well as any other variety. Climatic fluctuations, as well as cultural practices, soil type and fertility all have effects on yield. Cone uniformity with regard to size, weight, and level of maturity varies with the growing season. Cone shape is fairly uniform in the 'Millennium-48' variety.

The hop cones of 'Millennium-48' variety are well adapted to mechanical harvest because of their compactness and ovoid to conic shape. The cones do not shatter during harvest.

VII. Growth Characteristics

Growth of the annual stem is rapid during a relatively short thirty-five day period during which the bine will grow approximately 20–24 feet in length. The extent of this rapid growth is very dependent on temperature, soil conditions and cultural practices.

VIII. Variability of Botanical Characteristics

The dimensions of the various components of a hop plant, including stems, cones, leaves, laterals, and internodes vary tremendously from one year to the next, from one field to the next within the same year; and even from one plant to the next within the same field. Because of the variability of climate, temperature, soil conditions and cultural practices, this variation produces substantial overlapping of dimensions when comparing varieties and results in these dimensions having little use for comparing varieties.

IX. Propagation Methods

Asexual reproduction assures genetic stability and is used for increasing plant rootstock numbers to provide sufficient plants for commercial hop production. Sexual reproduction by plants of this variety is not possible because of its triploid genetic make-up. The asexual propagation methodology utilizes 2 inch stem cuttings, which are treated with a rooting hormone and rooted in potting media in greenhouses. The rooted cuttings are grown in greenhouses under controlled conditions including control of temperature, humidity, light intensity, and day length. The claimed plant produces true to type when asexually reproduced.

DETAILED DESCRIPTIVE INFORMATION

Following, is a detailed description of the botanical and analytical chemical characteristics of the new variety. The information for the botanical description was either collected or verified during the growing seasons of 1998 and 1999 in the growing area west of Toppenish, Wash. These botanical characteristics, and to a lesser degree the analytical chemical characteristics, are dependent on cultural practices and climatic conditions and can vary with location and season.

1. Parentage: A hop plant originating from a controlled cross pollination between a tetraploid 'Nugget' female hop plant with unpatented proprietary male hop plant '833-53M'.
2. Localities where grown and observed: Toppenish, Wash. and in the Willamette Valley, Oreg.
3. Dates of first and last harvest: Approximately September 10 and September 20, respectively, in Toppenish, Wash.; and September 10 and September 20, respectively, in the Willamette Valley of Oregon.
4. Plant characteristics:
   *Plant.*—Green vigorous, climbing vine.
   *Stripe.*—Green.
   *Stipule direction.*—90% up. 10% down.
   *Stipule size.*—Average 1.4 cm×2.4 cm. Range 1.2 cm×2.0 cm to 1.6 cm×2.9 cm.
   *Lateral leaf arrangement.*—Opposite, becoming alternate.
   *Number of leaf lobes.*—3 or 5 (mostly 5).
   *Leaf margin.*—Serrate to dentate.
   *Leaf size.*—Average 22.5×15.4 cm. Range 20.4 cm×13.5 cm to 23.5 cm×16.4 cm.
   *Aroma.*—Sweet, minty.
   *Yield.*—Range 2,300 to 2,700 pounds per acre.
5. Cone characteristics:
   *Bract tip shape.*—Cuspidate to mucronate.
   *Bract tip position.*—Loosely recurved.
   *Bracteole tip shape.*—Acute to rounded.
   *Compactness.*—Tight.
   *Shape.*—Conic.
   *Cone length.*—1.5 inches average.
   *Cone width.*—20.7 mm.
   *Cone tip shape.*—Pointed.
   *Strig.*—Thick.
   *Maturity.*—Late.
6. Color characteristics: Fall color characteristics are unknown because the leaves are totally removed and destroyed during the harvesting procedure. The following color characteristics for 'Millennium-48' have been determined. (Note: color numbers followed by an "A", "B"or "D" were determined using the Colour Chart of The Royal Horticultural Society of London, 1966; color numbers followed by a "C" were determined using the Pantone Color Specifier 747XR from the Pantone Library of Color No. 1).

*Immature leaf surface.*—143B.
*Leaf upper surface.*—147A.
*Leaf lower surface.*—148B.
*Bine background.*—144B.
*Bine stripe.*—144A.
*Cone bracteole.*—144B.
*Cone bract.*—137A.
*Sidearm stem.*—146B.
*Sidearm stripe.*—No stripe.
*Stipule.*—144B.
*Leaf (resin) gland.*—No significant color.
*Lupulin gland.*—12A.

7. Analytical data of cones:
   *% Alpha-acids (bale).*—12%–14% (ASBC Spectrophotometric method).
   *% Beta-acids (bale).*—3.8%–4.2% (ASBC Spectrophotometric method).
   *Alpha beta ratio.*—3.2–3.3.
   *Cohumulone (% of alpha-acids).*—Average 30.0%.
   *Colupulone (% of beta-acids).*—Average 57.0%.
   *Storage characteristics.*—23% transformation after 6 months at 22° C. (based on U.S.D.A. Hop Storage Index of baled hops). This rate of transformation is very comparable to that of the commercial varieties Galena and Nugget.
   *Total oils (mls/100 g).*—Average 2.3%.
   *Humulene (% of total oils).*—Average 27%.
   *Caryophyllene (% of total oils).*—Average 14.0%.
   *Humulene/caryophyllene ratio.*—Average 2.0.
   *Farnesene (% of total oils).*—Average 0%.
   *Myrcene (% of total oils).*—Average 40%. (Note: Analytical Data determined on hops with approximately 8% cone moisture.)
8. Disease resistance: The variety 'Millennium-48' is moderately susceptible to downy mildew, noting that complete resistance to the disease is not known to be available in any variety of hop. 'Millennium-48' is resistant to powdery mildew and tolerant to strains of Verticillium wilt and to the viruses found in the hops growing areas of the United States, as well as to the major soil-borne pests including Phytophthora root rot. All disease information is based on general field observations.
9. Regional adaptation: The 'Millennium-48' variety appears to be adapted to both the drier and the more humid growing regions of the United States, specifically including the Yakima Valley of Washington State and the Willamette Valley of Oregon State.
10. Ploidy: The mother is tetraploid and the father is diploid, thus making 'Millennium-48' a triploid plant. Because the variety is triploid, it is incapable of sexual reproduction. Reproduction can only be asexual.
11. Life expectancy: Lift expectancy of this variety is not known, but presumed to be theoretically indefinite similar to other varieties of the same species.
12. Use: Flavoring for beers, stouts and ales.
13. Virus and propagation status: 'Millennium-48' rootstock has been virus tested and is virus-free. Propagatable plant material exists.
14. Asexual reproduction: The plant reproduces true to type when asexually reproduced.

DISTINGUISHING CHARACTERISTICS

This new hop variety has been carefully compared to 'Nugget', the diploid variety from which the tetraploid female parent plant was derived. The hop industry does not make or rely on any comparisons between new varieties and their male parents because male hop plants lack the cones which make the female hop plants commercially valuable.

'Nugget' and 'Galena' are two publicly available hop varieties which are widely grown for commercial hop production in the Pacific Northwest of the United States. The alpha/beta ratio of 'Millennium-48' of 3.2 to 3.3 is significantly higher than that of either 'Nugget' (2.6) or 'Galena' (1.6). 'Millennium-48' also differs from 'Nugget' and 'Galena' for other analytical components of the cones, such as the humulene/carophyllene ratio.

'Millennium-48' differs from its siblings by having a lower content of alpha acids in the cone when growing under similar conditions.

What is claimed:

1. A new variety of hop plant substantially as herein shown and described.

* * * * *